United States Patent [19]
Sanders et al.

[11] Patent Number: 5,669,919
[45] Date of Patent: Sep. 23, 1997

[54] ANNULOPLASTY SYSTEM

[75] Inventors: Elliott H. Sanders, Westminster, Calif.; Carlos M. G. Duran, Missoula, Mont.

[73] Assignee: Medtronic, Inc., Minneapolis, Minn.

[21] Appl. No.: 700,620

[22] Filed: Aug. 16, 1996

[51] Int. Cl.⁶ ................................................. A61B 17/00
[52] U.S. Cl. ...................... 606/148; 606/139; 623/900; 623/2
[58] Field of Search ..................... 606/148, 139, 606/151, 153; 623/900, 2; 128/898

[56] References Cited

U.S. PATENT DOCUMENTS

| | | | |
|---|---|---|---|
| 4,667,673 | 5/1987 | Li | 606/153 |
| 5,041,130 | 8/1991 | Cosgrove et al. | 623/2 |
| 5,350,420 | 9/1994 | Cosgrove et al. | 623/2 |
| 5,476,510 | 12/1995 | Eberhardt et al. | 606/148 |
| 5,578,076 | 11/1996 | Krueger et al. | 623/900 |

FOREIGN PATENT DOCUMENTS

WO/92/12688  8/1992  WIPO ................................. 623/900

OTHER PUBLICATIONS

Baxter International, Inc. catalog article "Carpentier–Edwards Physio Annuloplasty Ring Mitral Model 4450", pp. 1–8.

*Primary Examiner*—Jeffrey A. Schmidt
*Attorney, Agent, or Firm*—Harry G. Weissenberger

[57] ABSTRACT

In annuloplastic surgery, the holder which supports the annuloplasty ring during the suturing of the ring to a heart valve annulus is released from its handle, and reattached for subsequent removal, without rotary or axially compressive stress on the holder. This is accomplished by inserting laterally movable locking tabs from the handle into the holder. The locking tabs are the ends of a Y-shaped clip which translates the axial movement of a locking button on the handle into a transverse holder-engaging movement.

4 Claims, 6 Drawing Sheets

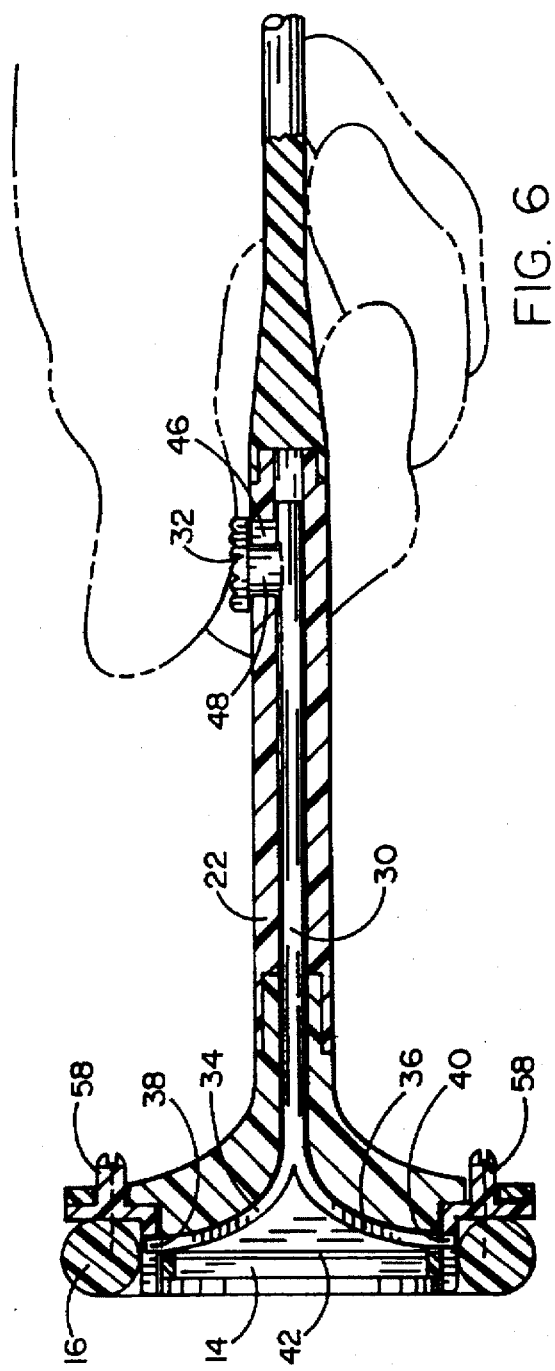
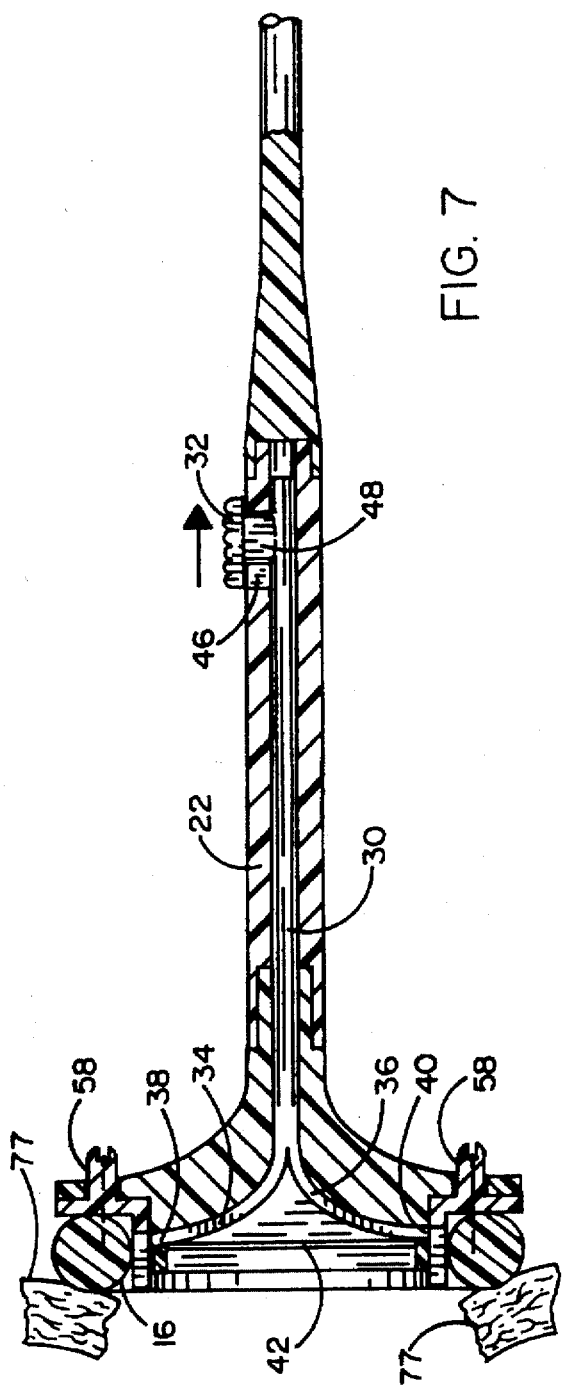

5,669,919

ANNULOPLASTY SYSTEM

FIELD OF THE INVENTION

This invention relates to devices for holding annuloplasty rings in place during surgery, and more specifically to a holder which can be released from, and reattached to, a handle without any rotary motion or axial pressure of the handle.

BACKGROUND OF THE INVENTION

The pumping action of a healthy human heart requires the proper opening and closing of heart valves such as the mitral and tricuspid valves as the heart beats. These valves consist of an annulus of cartilage-like tissue to which flexible leaflets are attached. The leaflets alternatively separate and come together to open and close the valves. Disease, injury or other factors sometimes cause the annulus to distend or enlarge so that the leaflets are pulled away from each other and cannot quite meet to close the valve. When this happens, blood leaks through the valve and the heart's pumping efficiency is impaired. If the leakage is serious, it becomes necessary to repair the valve by open-heart surgery.

The surgical procedure by which the annulus is brought back to its normal size and shape is known as annuloplasty. In that procedure, a nonelastic annuloplasty ring is placed into the position in which the annulus should be, and the annulus is sewn to it.

For the annuloplasty procedure, the ring is secured by sutures to a rigid plastic holder which maintains the ring in its proper shape (typically a partially flattened ellipse) during the procedure. The holder is in turn releasably secured to a bendable handle that can be formed by the surgeon to facilitate positioning of the ring and holder in the heart concentrically and coplanarly with the annulus of the valve to be repaired. Once the holder is placed and sutures initiated, the handle needs to be withdrawn in order to give the surgeon room to work and to properly see the annulus which is partly hidden by the septal shelf. Then, when the procedure is completed, valve closure is tested by injecting saline solution. The sutures which attach the ring to the holder are now cut, and the handle and holder are removed, leaving the ring in place.

A problem arises in the release and reattachment of the handle. Because the handle is bent, and because rotary stress on the holder and ring is undesirable, rotary movement (and, for that matter, axial movement also) of the handle during release and attachment must be minimized. The prior art has attempted to deal with this problem in various ways. For example, U.S. Pat. Nos. 5,041,130 and 5,350,420 to Cosgrove et al. disclose a releasable interlock using a pin and J-shaped slot which is released and engaged with a partially rotary, partially axial movement of the handle, while Baxter International, Inc.'s Model 4450 uses an axially engageable (but non-releasable) interlock.

Although the prior art devices were generally satisfactory, a need still existed for an annuloplasty device in which the handle and holder could be released and detached without any movement of the handle.

SUMMARY OF THE INVENTION

The present invention fills the above-mentioned need of the prior art by providing an attachment mechanism in which the motion of a flexible member axially movable inside the handle is translated into a movement, in a direction transverse to the handle, of locking the tabs which releasably engage the holder. The engaging and releasing functions are carried out by sliding a button along the side of the handle without moving either the handle or the holder.

In a further aspect of the invention, the bottom part of the handle, which engages the holder, carries markings which serve as a template to guide the surgeon in the proper placement of sutures along the ring.

BRIEF DESCRIPTION OF THE DRAWINGS

FIG. 6 is a vertical section of the system of this invention prior to the insertion of the ring into a heart valve annulus;

FIG. 7 is a vertical section similar to FIG. 6 but showing the clip in the position for releasing the holder following insertion of the ring;

DESCRIPTION OF THE PREFERRED EMBODIMENTS

Figure 4:
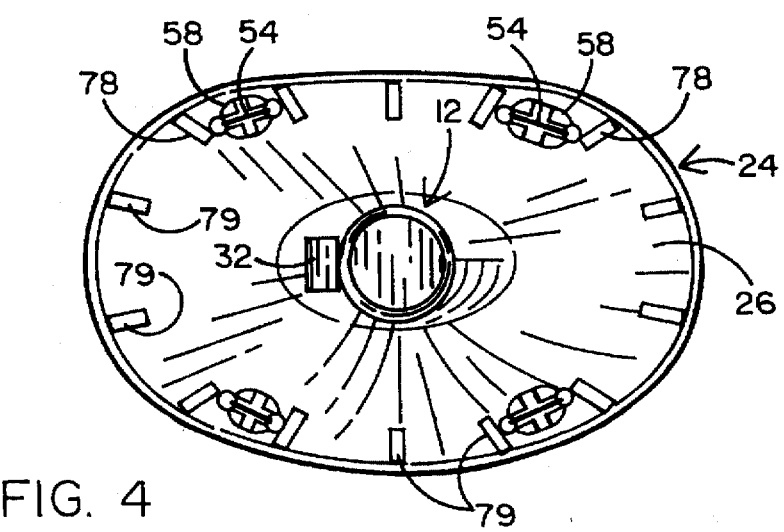
FIG. 4 is a plan view of the assembled handle and holder.

The exploded and perspective views of FIGS. 1 through 4 show the components of the inventive system. The system 10 includes a handle 12, a holder 14, and an annuloplasty ring 16. The handle 12 has a rigid grip portion 18, a malleable central portion 20, and a rigid control portion 22. The control portion 22 carries a head 24 to which the holder 14 can be releasably attached. The head 24 carries a template 26 (FIG. 4). The annuloplasty ring 16 is originally attached to the holder 14 and is eventually detached from it as the surgery proceeds.

The releasable attachment of the holder 14 to the handle 12 is accomplished by a resilient, flexible Y-shaped clip 28 positioned in the control portion 22. The shank 30 of the clip 28 is secured to a locking button 32 that can slide longitudinally on the outside of the control portion 22. The arms 34, 36 of the clip 28 are curved through a 90° arc so that their outer ends form locking tabs 38, 40 that move transversely outwardly of the head 24 when the button 32 and shank 30 are moved axially downwardly toward the head 24. Retaining flanges 51, 53 at opposing edges of the bottom face 42 of head 24 maintain the outer ends of arms 34, 36 in a common horizontal plane.

The operation of the system is illustrated by the detailed drawings of FIGS. 5 through 9. The handle 12 is first assembled by inserting the hollow shaft 44 of head 24 into the control portion 22 of handle 12 and securing it thereto. The locking button 32 is next inserted through slot 46 in portion 22 so that its flange 48 extends transversely through the interior of portion 22. The clip 28 is now inserted through head 24 and into portion 22 until its U-shaped end 50 slips over the flange 48 and becomes secured thereon by the protrusion 52. The resilient arms 34, 36 are then bent first inwardly, then outwardly as their locking tabs 38, 40 are inserted under the flanges 51, 53. This completes the assembly of the handle 12.

Figure 1:
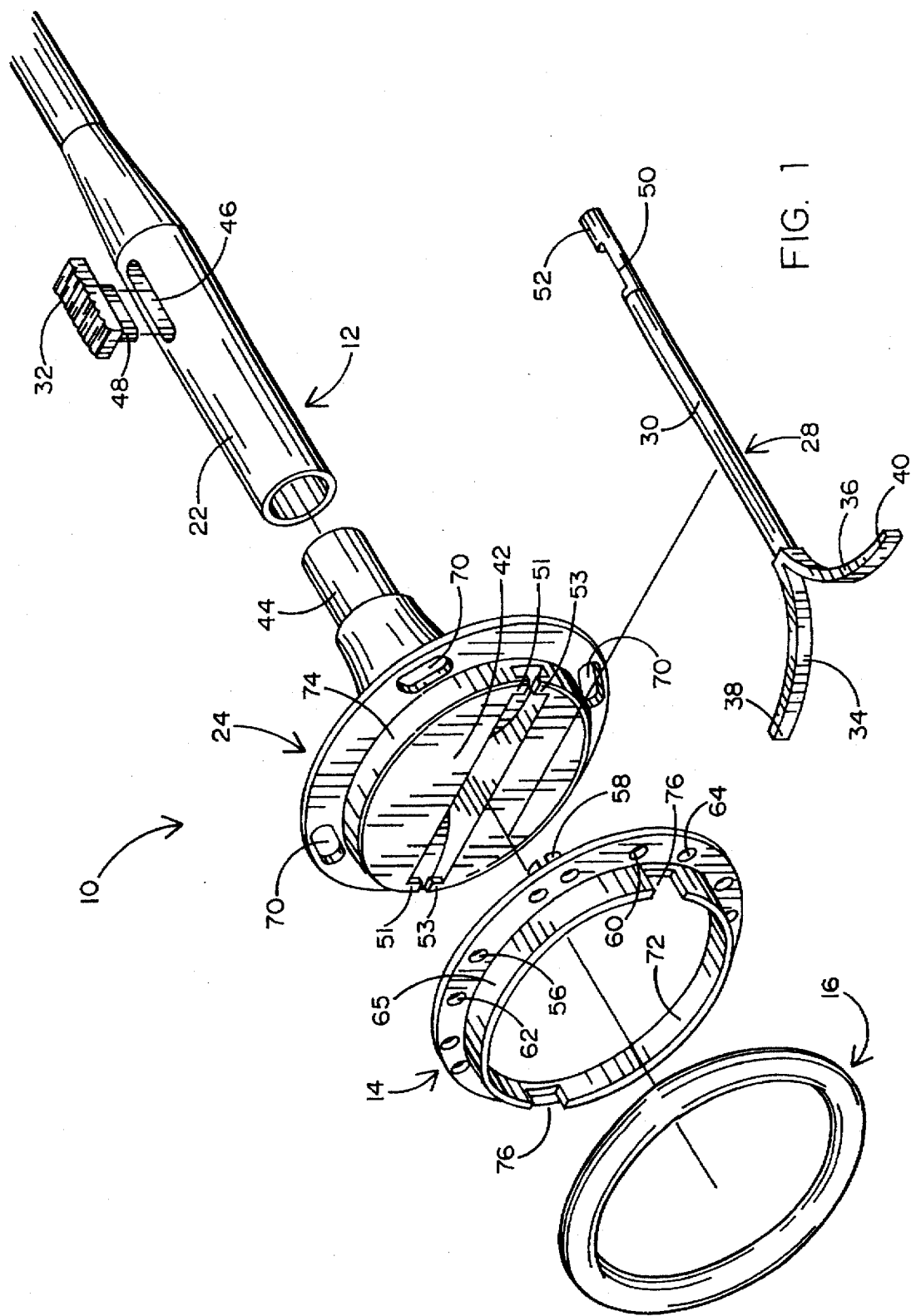
FIG. 1 is an exploded perspective view of the system of this invention.
Figure 2:
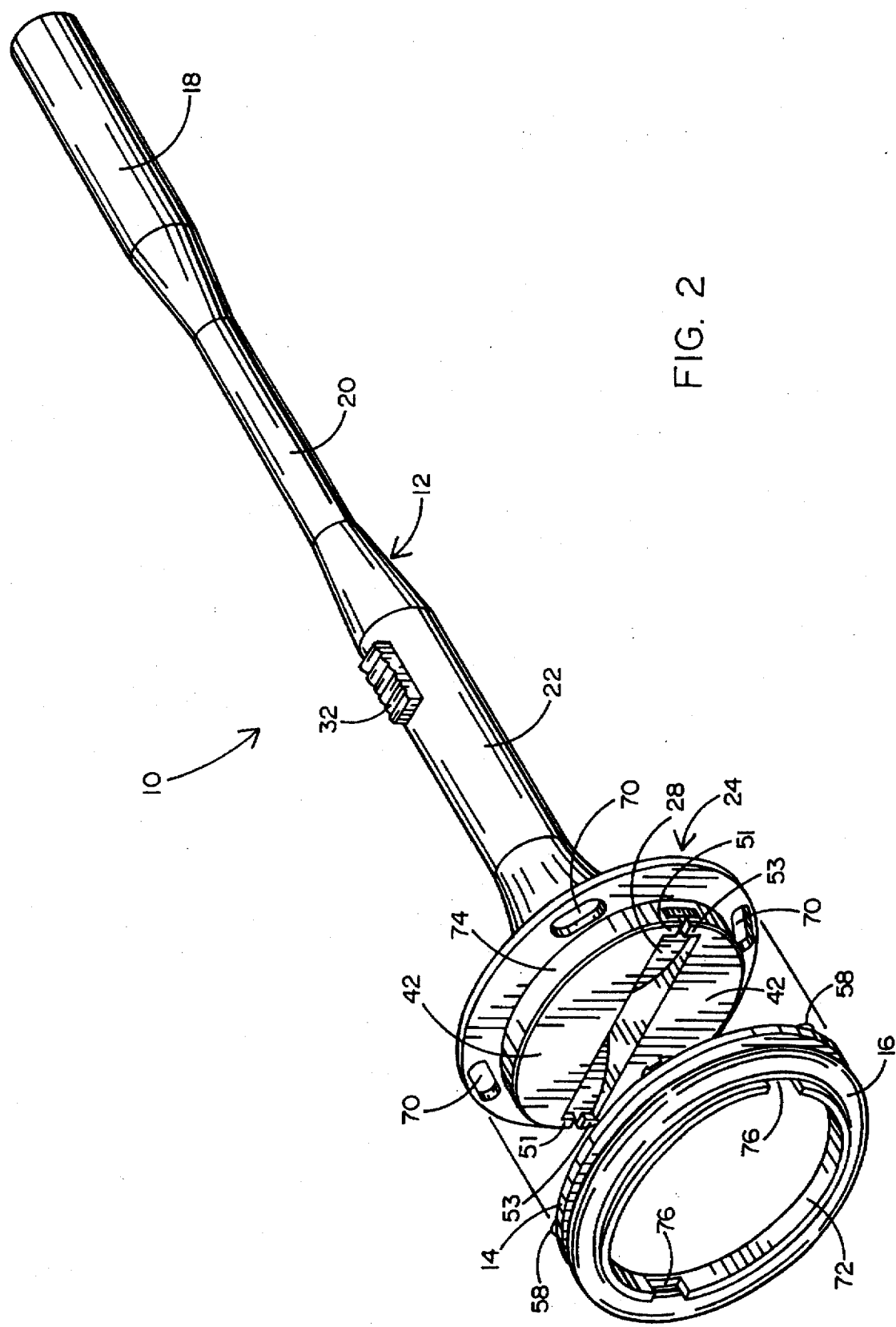
FIG. 2 is a perspective view of the handle separated from the holder and ring.
Figure 3:
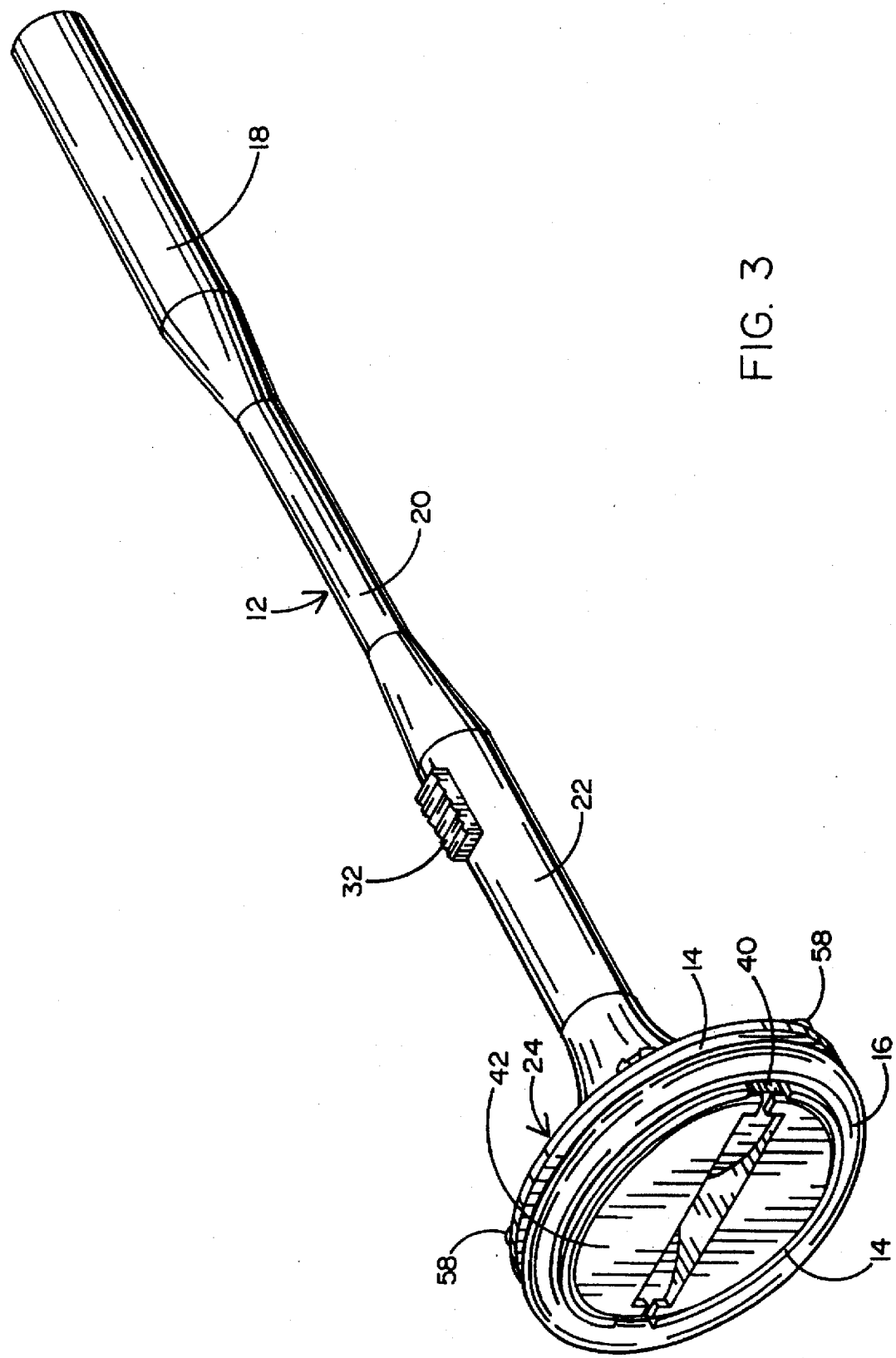
FIG. 3 is a perspective view of the handle assembled with the holder and ring.
Figure 5:
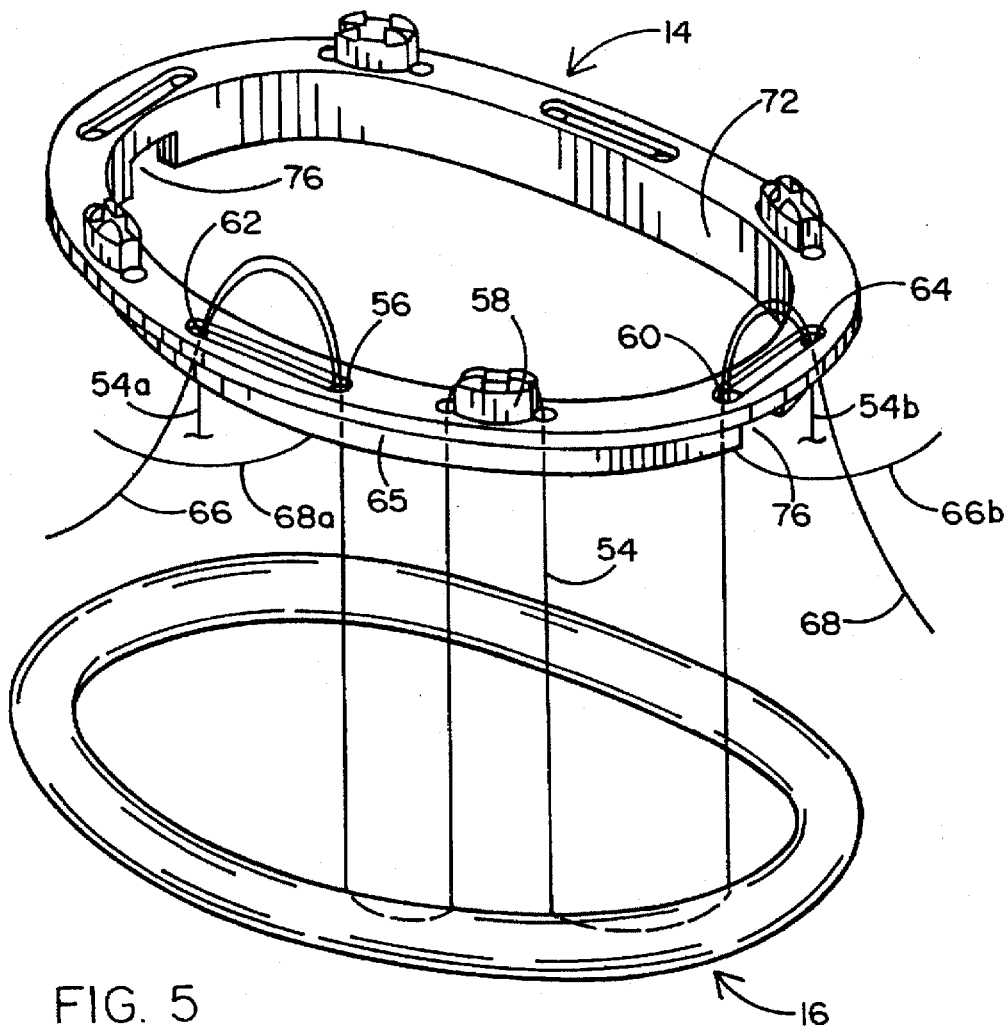
FIG. 5 is a perspective view of the holder and ring in the course of their assembly.

Prior to surgery, an annuloplasty ring 16 is sewn onto the holder 14 as best shown in FIG. 5. Sutures 54 (only one of four is fully shown in FIG. 5) are passed through opening 56 in holder 14, ring 16, over the cutting guide post 58, through the ring 16 again, and finally through opening 60 in holder 14. The loose ends of adjacent sutures 54 may be passed through openings 62, 64 so as to form a complete loop circuit when the loose ends are tied, thereby ensuring removal of all suture strands. The sutures 54 are pulled tight so that the ring 16 lies snugly against the surface 65 on the underside of the holder 14 (FIGS. 2, 3 and 6–8), and the loose ends 66, 68 are then tied to the loose ends 68a and 66b, respectively, of adjacent strands 54a and 54b. The smooth surface 65 prevents bunching of the ring 16 when the surgical sutures 69 are tied off, which can cause a problem with some prior art holder designs.

The holder 14 carrying the ring 16 is now attached to the handle 12 by so placing it against the underside of head 24 so that the posts 58 engage and protrude through the openings 70 formed in the template 26. The inner surface 72 of holder 14 then lies against the guide flange 74 of the head 24. At this time, with the locking button 32 in its upper position in slot 46, the tabs 38, 40 of the locking clip 28 are retracted inside the guide flange 74.

When the holder 14 is in place on head 24, the button 33 is pushed down in slot 46. This causes the tabs 38, 40 to be extended laterally through guide flange 74 and to lockingly engage the recesses 76 of holder 14. This secures the holder 14 to the handle 12 (FIG. 6).

Figure 8:
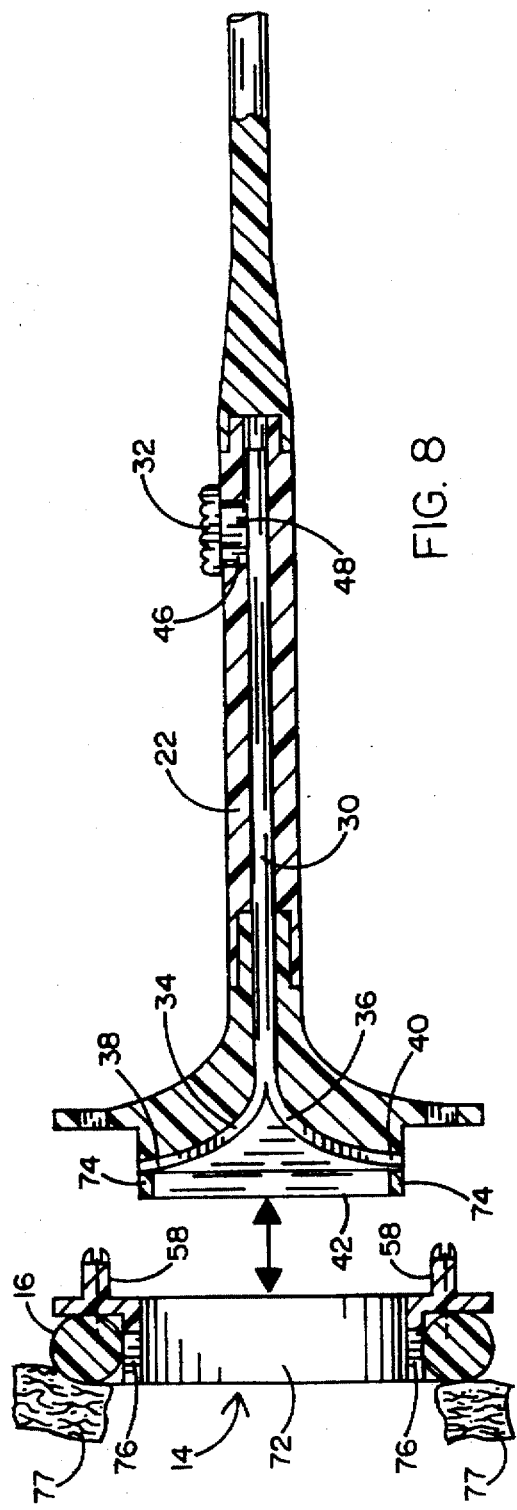
FIG. 8 is a vertical section illustrating the withdrawal and eventual reinsertion of the handle.
Figure 9:
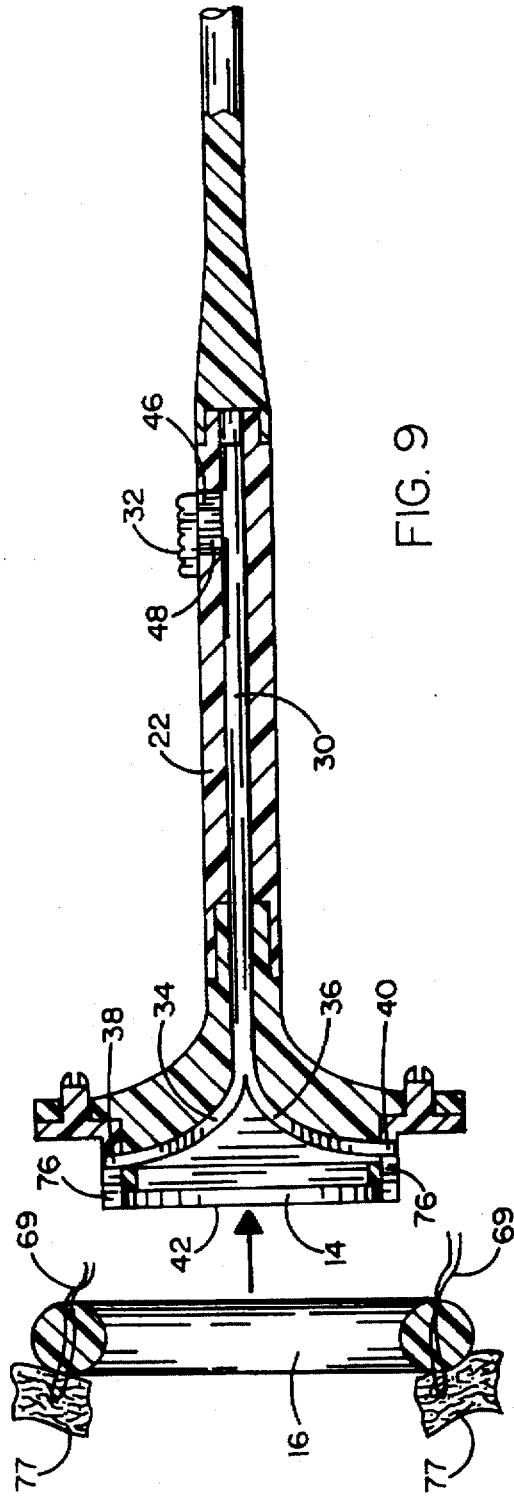
FIG. 9 is a vertical section showing the removal of the holder upon completion of the surgery.

In the course of the surgery, the surgeon uses the handle 12 to place the holder 14 and ring 16 into the appropriate position in the patient's heart. The ring is now sutured to the heart valve annulus 77 in a conventional manner in a few accessible places under the guidance of the long suture markings 78 on the template 26 (FIG. 4). The markings 78 pinpoint the locations of the trigones, or cartilage anchors, of the annulus which are preferred suture locations. The shorter markings 79 indicate suggested positions for other sutures. At this point, it is desirable to remove the handle 12 to facilitate the surgeon's access to the ring 16 for completing the suturing of the ring 16 to the heart valve annulus. This is done by pulling the button 32 upwardly so as to cause tabs 38, 40 to retract into the guide flange 74 and release the holder 14 (FIG. 7). The handle 12 can now be pulled away from the holder 14 (FIG. 8).

When the suturing of the ring 16 to the heat valve annulus has been completed, and the heart valve has been conventionally tested by an injection of saline, the holder 14 can be removed. This is done by reinserting the handle 12 (FIG. 8) and locking the holder 14 to the handle 12 by pushing the button 32 down. The sutures 54 holding the ring 16 to the holder 14 are now cut at the protruding cutting guide posts 58, and the handle 12 and holder 14 are pulled out of the heart (FIG. 9), thereby pulling the sutures 54 out of the ring 16.

It will be seen from the foregoing that neither the attachment of the holder 14 to the handle 12, nor its release from handle 12, involve any rotary movement nor any axial pressure of handle 12 against the holder 14. Consequently, the system of this invention avoids any stress to the heart valve annulus or to the sutures which tie it to the annuloplasty ring 16.

It is understood that the exemplary annuloplasty system described herein and shown in the drawings represents only a presently preferred embodiment of the invention. Indeed, various modifications and additions may be made to such embodiment without departing from the spirit and scope of the invention. Thus, other modifications and additions may be obvious to those skilled in the art and may be implemented to adapt the present invention for use in a variety of different applications.

We claim:

1. An annuloplasty holder system, comprising:
    a) a holder adapted to hold an annuloplasty ring;
    b) a handle having an end arranged to be releasably engaged with said holder;
    c) a plurality of tabs on said handle, said tabs being movable transversely of said handle and being arranged to releasably lockingly engage said holder when moved transversely outwardly of said handle;
    d) a tab moving member positioned on said handle, said tab moving member being longitudinally movable with respect to said handle and arranged to move said tabs transversely to engage said holder when said tab moving member is longitudinally moved; and
    e) an actuating member on the outside of said handle connected to said tab moving member for moving the same.

2. The system of claim 1, in which said tab moving member is a flexible, substantially Y-shaped element, said tabs being formed on the ends of the branches of the Y, and the branches of said Y-shaped element being bent to move transversely of said handle when the stem of the Y is moved longitudinally of said handle.

3. The system of claim 1, in which said handle has a malleable portion and a rigid portion, said tab moving member and said actuating member being positioned in said rigid portion.

4. The system of claim 1, in which said handle carries at its holder-engaging end a template marking the locations for proper placement of sutures on said annuloplasty ring.

* * * * *